United States Patent [19]
Knoll et al.

[11] 3,969,519
[45] July 13, 1976

[54] PHARMACEUTICAL COMPOSITION HAVING SYNERGISTIC ANALGESIC ACTIVITY AND CONTAINING AZIDOMORPHINE OR AZIDOCODEINE

[75] Inventors: József Knoll; Zsuzsanna Fürst; Zoltán Mészaros; Gábor Nagy; Ágoston Dávid, all of Budapest; Rezsö Bognár; Sándor Makleit, both of Debrecen; Gyula Valovics, Tiszavasvari, all of Hungary

[73] Assignee: Chinoin Gyogyszer es Vegyeszeti, Budapest, Hungary

[22] Filed: Dec. 26, 1974

[21] Appl. No.: 536,402

[30] Foreign Application Priority Data
Dec. 29, 1973 Hungary.............................. CI 1432

[52] U.S. Cl................................. 424/251; 424/260
[51] Int. Cl.² ............... A61K 31/505; A61K 31/485
[58] Field of Search............................ 424/251, 260

[56] References Cited
OTHER PUBLICATIONS
Chinon–Chem. Abst. vol. 75 (1971) p. 5939w.
Bognar et al.–Chem. Abst. vol. 71 (1969) p. 13243x.

*Primary Examiner*—Sam Rosen
*Attorney, Agent, or Firm*—Karl F. Ross; Herbert Dubno

[57] ABSTRACT

A pharmaceutical composition having synergistic analgesic effect which includes an azido compound of the formula:

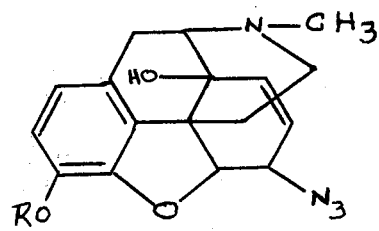

namely an azido morphine or an azido codeine, and at least one compound of the formula:

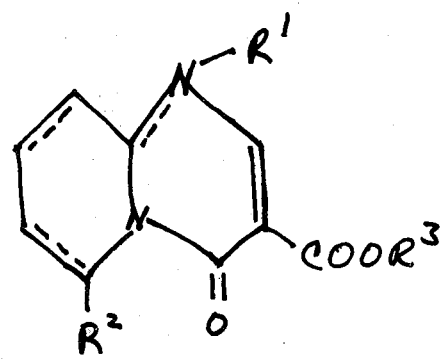

the synergistic composition has been found to have less narcotic side effects than morphine and equal or better analgesic properties.

14 Claims, 1 Drawing Figure

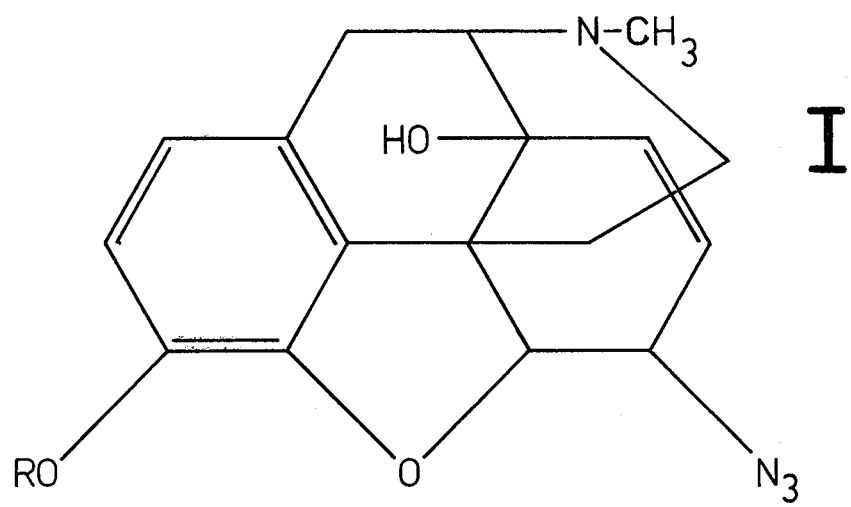
I
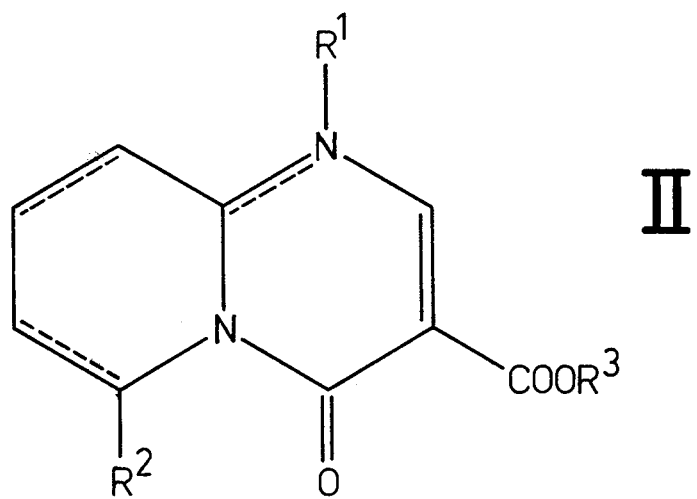
II

PHARMACEUTICAL COMPOSITION HAVING SYNERGISTIC ANALGESIC ACTIVITY AND CONTAINING AZIDOMORPHINE OR AZIDOCODEINE

The present invention relates to pharmaceutical compositions having synergetic analgetic activity and a process for the preparation thereof. For the relief of postoperational pain and in the case of cancer patients in an advanced stage of the disease morphine and its derivatives are the most frequently used efficient analgesics. It is a wellknown fact, however, that in patients treated with morphine, the harmful side-effects, e.g. respiratory depression, tolerance and dependence develop in a relatively short time. The patient gets used to morphine and rapidly rising doses are required to obtain an equinanalgetic effect; tolerance or dependence develops and the patient is in permanent need of the euphorizing effect of morphine. Another disadvantage of morphine is the fact that it is practically ineffective on oral application. All the analgesics suited for the treatment of unbearable pain (e.g. cancer, postoperative, infraction, lithiases, etc.) are likely to induce the development of tolerance on chronic administration and their withdrawal produces severe — often fatal — somatic and psychic symptoms (physical and psychic dependence). It is generally accepted (Martin, 1967, Pharm. Rev. 19, 463) that the apperance of tolerance and dependence necessarilly accompany the action of the morphine type drugs on the analgesic receptors. An analgesic equipotent to morphine, but devoid of its narcotic side-effects, has for long been needed in clinical practice. For the replacement of morphine 6-desoxy-6-azido14-hydroxy-dihydro-isomorphine, prepared by Bognar and Makleit seems to be suitable. According to the present invention there are provided pharmaceutical compositions having synergestic analygesic effect comprising at least one compound of the formula I or a salt thereof (wherein R is hydrogen or methyl) and at least one compound of the formula II (wherein $R^1$ and $R^2$ are lower alkyl and $R^3$ is hydrogen or lower alkyl) in admixture with pharmaceutically acceptable inert solid or liquid carriers or diluents.

The present invention is based on the recognition that the compounds of the formula II and their salts and quaternary salts potentiate the analgesic action of the azido compounds of the formula I to a significant extent and also have an advantageous influence on their other properties. Thus, a well-expressed potentiation takes place and the effect of the combination surpasses the additive effect of the components when used alone. A further advantage resides in the fact that the combinations according to the present invention are devoid of narcotic side effects.

In the compositions of the present invention a compound of the formula I preferably 14-hydroxy-azidomorphine may be used, but 14-hydroxy-axido-codeine may be applied with similar results too. The compound of the formula I may be used as the free base or in the form of an acid addition salt thereof. The salts may be those formed with inorganic or organic acids; the acid component used must be pharmaceutically acceptable and should provide preferably solubility properties to the salt obtained. The bitartarate salts of the compounds of the formula I possess particularly advantageous solubility characteristics.

In the compounds of the formula II the alkyl groups may be straight or branched chained and contain 1–6, preferably 1–4 carbon atoms (e.g. methyl, ethyl, n-propyl, isobutyl, etc.). The salts and quaternary salts of the compounds of the formula II may contain any pharmaceutically acceptable anion (e.g. inorganic anions, such as nitrate, chloride, bromide or sulphate anion; and organic anions, e.g. methylsulphate, ethylsulphate, etc.). A particularly preferred representative of the compounds of the formula II is the 1,6-dimethyl-3-carbethoxy-4-oxo-6,7,8,9-tetrahydro-homopyrimidazolium-methosulphate.

Synergistic analgesic effect is measured on the one hand by means of the analgesis tests (Knoll et al: Animal and Clinical Pharm. Techn. in Drug Ev. (1967) 305–321). This is a model test for surgical pains and demonstrates exclusively a major analgesic effect. The essence of the test is that under the effect of a 10 mg/kg i.v. dose of morphine, rats can be subjected to laparatomia without the slightest signs of pain. For each dose 10 rats each were used.

It has been found that the homopyrimidazole derivatives of the formula II and salts and quaternary salts thereof on the one hand, and the 14-hydroxy-azidomorphine and 14-hydroxy-azido-codeine on the other, potentiate the analgesic effect of each other to a significant extent without influencing the toxicity or other side effects. The present invention is based on the recognition that a mutual effect exists between the representatives or both compound-groups. The synergistic effect is shown on the examples of a composition cobtaining 14-hydroxy-azido-morphine and 1,6-dimethyl-3-carbethoxy-4-oxo-6,7,8,9-tetrahydro-homopyrimidazolium-methosulphate by using the algolytic test discussed above. The results are summarized in the following table:

Table I

| Compound A | Route of administration | Compound B | Route of administration | Algolytic test analgetic effect in % |
|---|---|---|---|---|
| 0.050 | i.v. | — | — | 15 |
| — | — | 75 | i.v. | 2 |
| 0.050 | i.v. | 75 | i.v. | 81 |
| 10 | p.o. | — | — | 18 |
| — | — | 250 | p.o. | 9 |
| 10 | p.o. | 250 | p.o. | 69 |

It appears from the data of the above table that both on intravenous and oral administration the combination containing doses of the components being ineffective per se (0.050 mg/kg) of compound A i.v. and 75 mg/kg i.v. of compound B, or 10 mg/kg p.o. of compound A and 250 mg/kg p.o. of compound B respectively produces a very strong analgesic effect being 81% in intravenous and 69% in oral administration. The algolytic test is a measure exclusively of the analgesic effect of narcotics. For this reason, the said composition of the present invention may be very valuable in the relief of surgical pains. The synergistic effect of the pharmaceutical composition of the present invention is also proved by the hot-plate test, described by Woolfe and McDonald (J. Pharm. 80, 300) and modified by Porszasz and Herr (Kiserl. Orvostud 2, 292). This method is based on the measurement of radiating heat. The essence of the test is that rats without preliminary training are placed on plates having a temperature of 56°C and after a certain period, the time of appearance of certain pain reactions (blowing and licking of the paws) is measured. The analgesic effect is expressed in the percental prolongation of the reaction time of the control.

Table II

| Compound A | Route of administration | Compound B | Route of administration | Hot plate test analgesic effect in % |
|---|---|---|---|---|
| 0.025 | i.v. | — | — | 29 |
| — | — | 50 | i.v. | 14 |
| — | — | 75 | i.v. | 49 |
| 0.025 | i.v. | 50 | i.v. | 68 |
| 0.025 | i.v. | 75 | i.v. | 97 |
| 10.0 | p.os | — | — | 21 |
| — | — | 250 | p.os | 32 |
| 10.0 | p.os | 250 | p.os | 92 |

It may be seen from the above table that the homopyrimidazole-derivative increases analgesic effect of compound A to a significant extent. This is well proved by the experiment in which the two compounds are added simultaneously intravenously (0.025 mg/kg and 50 mg/kg respectively) or orally (10 mg/kg and 250 mg/kg respectively). From the point of view of practical therapy the latter may be of great importance, since it is well-known the derivatives of morphine when administered orally, show low activity and the strong peroral assuaging of pain is an undissolved problem. The effective intravenous combinations may be used in operation narcosis and the introduction thereof. The mutual effect between azidomorphine derivatives and homopyrimidazole derivatives has been demonstrated in several pharmacological tests. In pain relief, a potentiating synergism has been proved. Furtheron, it has been shown that the synergism of the analgesic effect is not accompanied by a synergism of undesired side-effects (e.g. central nerval depressive effect).

The central nerval depressive effect is tested on the modified spring test (J. Knoll: Publications of the Hungarian Academy of Sciences 14, 223). In earlier publications (Knoll, 1967; Screening and grouping of psycho-pharmacologic agents in: Animal and Clinical Pharm.Techn. in Drug Ev. 2, Ed.s.: Siegler, P. E. and Moyer, J. H. Year Book Medical Publ. Chicago, 1967. pp. 305-321.: Knoll et al: 1967, Arzneimittelforschung 21, (1971) 717-738) we have pointed out that while in the modified spring test morphine derivatives inhibit the defence reaction and escape of the animals when administered already in therapeutical doses exerting analgesic effect, the homopyrimidazoles exhibit said effect but in sub-toxical doses. The synergistic combinations were tested under subcutaneous and oral administration. The mutuality and many-sidedness of the synergism was determined too. The results are summarized in the following table:

Table III

| Compound A mg/kg | Route of administration | Compound B mg/kg | Route of administration | Activity | % index |
|---|---|---|---|---|---|
| 0.025 | s.c. | — | — | 0 | 8 |
| — | — | 50 | s.c. | 0 | 7.6 |
| 0.025 | s.c. | 50 | s.c. | 20 | 6.2 |
| 5 | p.os | — | — | 0 | 8.8 |
| — | — | 150 | p.os | 0 | 8.8 |
| 5 | p.os | 150 | p.os | 40 | 5.0 |

Thus in the modified spring test the combination of 14-hydroxy-azido-morphine and 1,6-dimethyl-4-oxo-3-ethoxycarbonyl-6,7,8,9-tetrahydro-homopyrimidazolium-methosulphate results a simple addition of the effect of the components in the place of the synergistic effect potentiating observed in the analgesic effect.

Similarly to 14-hydroxy-azido-morphine, a synergism has been demonstrated with the combination of 14-hydroxy-azido-codeine and 1,6-dimethyl-3-carbethoxy-4-oxo-6,7,8,9-tetrahydro-homopyrimidazolium-methosulphate too. The results are summarized in the following table:

Table IV

| Compound C mg/kg | Route of administration | Compound B mg/kg | Route of administration | Hot plate test % | Modified spring test % | index |
|---|---|---|---|---|---|---|
| 0.25 | s.c. | — | — | — | 20 | 6.2 |
| 0.5 | s.c. | — | — | 17 | — | — |
| 1.0 | s.c. | — | — | 35 | — | — |
| — | — | 50 | s.c. | 13 | — | — |
| — | — | 75 | s.c. | 49 | 20 | 5.6 |
| 0.5 | s.c. | 50 | s.c. | 86 | — | — |
| 0.125 | s.c. | 75 | s.c. | — | 20 | 6.2 |
| 0.125 | s.c. | 100 | s.c. | — | 40 | 4.6 |
| 2.5 | p.os | — | — | — | 0 | 8.2 |
| 3.75 | p.os | — | — | — | 0 | 6.8 |
| 5.0 | p.os | — | — | — | 40 | 5.2 |
| 2.5 | p.os | 50 | p.os | — | 0 | 8.2 |
| 2.5 | p.os | 100 | p.os | — | 50 | 4.4 |

The values of the above table show a synergism of analgesic effect similar to 14-hydroxy-azido-morphine (14-hydroxy-azido-codeine, 0.5 mg/kg s.c. and 50 mg/kg of compound B s.c.), while the central depressive effect of the combination does not exceed the additive effect of the components.

In the following test compound B has been replaced by the following representative derivatives of the homopyrimidazole compounds of the formula II.

| | |
|---|---|
| Compound A = | 14-hydroxy-azido-morphine |
| Compound B = | 1,6-dimethyl-3-ethoxycarbonyl-4-oxo-6,7,8,9-tetrahydro-homopyrimidazolium-methosulphate |
| Compound C = | 14-hydroxy-azido-codeine |
| Compound D = | 1,6-dimethyl-3-ethoxycarbonyl-4-oxo-1,6,7,8,9,10-hexahydro-homopyrimidazole |
| Compound E = | 6-methyl-3-ethoxycarbonyl-4-oxo-6,7,8,9-tetrahydro-homopyrimidazole |
| Compound F = | 1,6-dimethyl-3-ethoxycarbonyl-4-oxo-6,7,8,9-tetrahydro-homopyrimidazole. |

The results obtained are summarized in the following table.

Table V

| Compound A mg/kg | Compound B mg/kg | Homopyrimidazole Compound | Dose | Hot plate Test % |
|---|---|---|---|---|
| 0.025 i.v. | — | — | — | 29 |
| — | — | E | 200 i.v. | 20 |
| — | — | — | 300 i.v. | 72 |
| 0.025 i.v. | — | E | 200 i.v. | 39 |
| — | — | F | 300 i.v. | 24 |
| — | — | — | 400 i.v. | 61 |
| 0.025 i.v. | — | F | 300 i.v. | 48 |
| — | — | D | 50 i.v. | 39 |
| 0.025 i.v. | — | D | 50 i.v. | 52 |
| — | 0.5 s.c. | — | — | 17 |
| — | — | E | 200 s.c. | 27 |
| — | 0.5 s.c. | E | 200 s.c. | 26 |
| — | — | D | 50 s.c. | 22 |
| — | 0.5 s.c. | D | 50 s.c. | 55 |
| — | — | F | 300 s.c. | 28 |
| — | 0.5 s.c. | F | 300 s.c. | 27 |

The above data show that synergism is also present in combinations comprising a compound of the formula I and a compound of the formula II other, than compound B, but the best results were achieved when using compositions containing a compound of the formula I and 1,6-dimethyl-3-carbethoxy-4-oxo-6,7,8,9-tetrahydro-homopyrimidazolium-methosulphate. A further advantage of the composition of the present invention is that the central depressive effect of the composition does not surpass the additive effect of the components. The homopyrimidazole derivatives of the formula II and salts and quaternary salts thereof and also the preparation of these compounds is described in our British Pat. No. 1,209,946. The relative amount of the active ingredients in the combination according to the present invention may vary between wide ranges. It may be stated that the composition may contain about 20–1000, preferably 100–1000, particularly 300–1000 parts by weight of a compound of the formula II related to 1 part by weight of an azidocompound of the formula I. In oral parenteral compositions the said ratio may be about 100:1–1000:1, while in oral compositions about 20:1–100:1. The pharmaceutical compositions of the formula I may be finished in dosage forms suitable for oral or parenteral administration. The oral forms may be tablets, capsules, pills, coated pills, etc., while the parenteral dosage forms may be injectable preparations, powder ampouls, etc. The pharmaceutical compositions of the present invention comprising 14-hydroxy azido-codeine or a salt thereof as compound of the formula I are suitable for oral administration (tablets, capsules too. This oral dosage form is particularly advantageous, since in the clinical practice of analgesics of morphine type it enables the elimination of the injection treatment, being very uncomfortable and painful, for the first time. The said oral composition comprises preferably about 20–100 parts by weight, particularly preferably 30 parts by weight of a compound of the formula II calculated on 1 part by weight of azido-compound or the bitartarate thereof. A highly preferred embodiment of the present invention is a tablet or capsule comprising about 100–250 mg. particularly 150 mg., of 1,6-dimethyl-3-carbethoxy-4-oxo-6,7,8,9-tetrahydro-homopyrimidazolium-methosulphate and 2,5–10 mg., preferably 5 mg of 14-hydroxy-azido-codeine on the bitartarate thereof.

The parenteral compositions according to the present invention contain preferably 100–1000 parts by weight of a compound of the formula II related to 1 part by weight of an azido-compound of the formula I.

A very preferred embodiment of the present invention is a parenteral composition (injectable solution, powder ampouls/ comprising about 75–500 mg of 1,6-dimethyl-3-carbethoxy-4-oxo-6,7,8,9-tetrahydro-homopyrimidazolium-methosulphate and about 0.2–0.5 mg of azido-derivative.

The synergistic compositions of the present invention may be prepared by methods of the pharmaceutical industry known per se. The compositions for oral administration may be prepared by admixing the active ingredient with inert non-toxic carriers or diluents (e.g. cellulose, silicic acid, stearine, polyvinylpyrrolidone, talk, starch, etc.). The said compositions may also contain the well-known additives/e.g. emulsifying, suspending agents, dyes, salts for controlling the osmotic pressure, buffers, etc.).

The parenteral compositions of the present invention may be prepared in aqueous or non-aqueous medium. The non-aqueous preparations may be prepared in propylene glycol, polyethylene glycol or any other suitable solvents. Powder ampoules may be prepared preferably by introducing a homopyrimidazole derivative of the formula II into a powder ampoule, dissolving an azido-compound of the formula I in distilled water or in a suitable non-aqueous medium, in a solvent ampoule and dissolving a homopyrimid-azole derivative of the powder ampoule before use in the content of the solvent ampoule.

The preferred dosage in human therapy amounts to 1 capsule or one injection described above. The total daily dosage may consist of three or four single doses as defined above. These data are, however, mainly of informative character, and the dosage used may be lower or higher, than the said data depending on the circumstances of the given case, the condition of the patient and the prescription of the physician.

Further details of our invention are to be found in the Examples, without limiting the scope of our invention to the Examples.

EXAMPLES 1. 500 mg of 1,6-dimethyl-3-carbethoxy-4-oxo-6,7,8,9-tetrahydro-homopyrimidazolium-methosulphate are filled into a powder ampoule. 0.5 mg. of 14-hydroxy-azido-morphine bitartarate are dissolved in 5 ml of distilled water. Before use, the homopyrimidazole derivative being present in the powder ampoule is dissolved in the contents of the solvent ampoule. The composition is suitable for intravenous administration. In use at surgical intervention the proposed dose is one ampoule.

| 2. | |
|---|---|
| 1,6-dimethyl-3-carbethoxy-4-oxo-6,7,8,9-tetrahydro-homopyrimidazolium-methosulphate | 75 mg |
| 14-hydroxy-azido-morphine-bitartarate | 0.5 mg |
| Distilled water ad q.s. | 2 ml. |

3. A parenteral preparation having the following composition is prepared:

| 3. A parenteral preparation having the following composition is prepared: | |
|---|---|
| 1,6-dimethyl-3-carbethoxy-4-oxo-6,7,8,9-tetrahydro-homopyrimidazolium-methosulphate | 150 mg |
| 14-hydroxy-azido-morphine-bitartarate | 0.5 mg |
| Propylene glycol | 0.66 ml |
| Polyethylene glycol | 0.66 ml |
| Cellosolve | 0.66 ml |

The injectable solution thus obtained is filled into ampoules. The solution thus obtained is very stable; during storage at 20°C for 5 years, the decomposition is but a few per cent.

4. According to known methods of pharmaceutical industry, capsules having the following composition are prepared:

| | |
|---|---|
| 14-hydroxy-azido-codeine | 5 mg |
| 1,6-dimethyl-3-carbethoxy-4-oxo-6,7,8,9-tetrahydro-homopyrimidazolium-methosulphate | 150 mg |
| Colorant (dye) | 1 mg |
| Titanium dioxide | 3 mg |
| Betaine hydrochloride | 3 mg |
| Colloidal silicic acid | 13 mg |
| Polyvinylpyrrolidone | 15 mg |
| Stearine | 26 mg |
| Crystalline cellulose | 76 mg |

What we claim is:
1. A pharmaceutical composition of synergistic analgesic effect which comprises in effective amounts at least one azido-compound of the formula

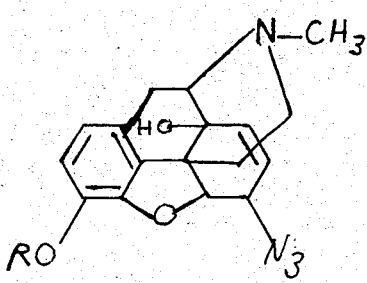

or its salt, wherein R is hydrogen or methyl and at least one homopyrimidazole compound of the formula:

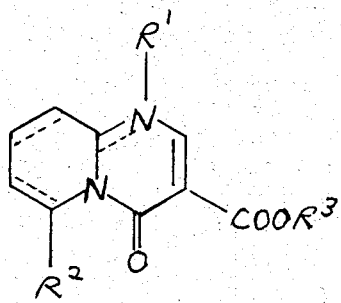

wherein $R^1$ and $R^2$ are lower alkyl and $R^3$ is hydrogen or lower alkyl, and the dotted lines represent either double bonds or hydrogen atoms or a salt or pharmaceutically acceptable quaternary salt thereof in admixture with pharmacetically acceptable carriers or diluents.

2. The pharmaceutical composition defined in claim 1 which comprises the azido compound in the form of its bitartarate.

3. The pharmaceutical composition defined in claim 1 which comprises as the homopyrimidazole compound 1,6-dimethyl-3-carbethoxy-4-oxo-6,7,8,9-tetrahydrohomopyrimidazolium methosulfate.

4. The pharmaceutical composition defined in claim 1 which comprises 100 to 1000 parts by weight of the homopyrimidazole compound or its pharmaceutically acceptable salts relative to 1 part by weight of the azidocompound or its salt.

5. The pharmaceutical composition defined in claim 4 which comprises 300 to 1000 parts by weight of the homopyrimidazole compound or its pharmaceutically acceptable salts.

6. The pharmaceutical composition defined in claim 4 wherein the pharmaceutically acceptable salts are quaternary ammonium salts.

7. The pharmaceutical composition defined in claim 1 in a form suitable for parenteral administration.

8. The pharmaceutical composition defined in claim 7 in the form of an injectable preparation of a powder ampoule.

9. The pharmaceutical composition defined in claim 1 which comprises 20 to 100 parts by weight of the homopyrimidazole or its quaternary salts relative to 1 part by weight of 14-hydroxy-azido-codeine or its salts.

10. The pharmaceutical composition defined in claim 9 which comprises 25 to 50 parts by weight of the homopyrimidazole or its quaternary salts.

11. The pharmaceutical composition defined in claim 9 wherein the homopyrimidazole is 1,6-dimethyl-3-carbethoxy-4-oxo-6,7,8,9-tetrahydropyrimidazolium-methosulfate.

12. The pharmaceutical composition defined in claim 1 in a form suitable for oral administration.

13. The pharmaceutical composition defined in claim 12 in the form of tablets or capusles.

14. A method of relieving pain in humans which comprises orally, intravenously or subcutaneously administering to the patient a pharmaceutical composition as defined in claim 1.

* * * * *